United States Patent
Tomita et al.

(10) Patent No.: US 9,867,927 B2
(45) Date of Patent: Jan. 16, 2018

(54) CARRIER FOR BLOOD COMPONENT ADSORPTION AND BLOOD COMPONENT ADSORPTION COLUMN

(75) Inventors: Naotoshi Tomita, Otsu (JP); Yoshiyuki Ueno, Otsu (JP); Kazuhiro Tanahashi, Otsu (JP)

(73) Assignee: Toray Industries, Inc. (JP)

( * ) Notice: Subject to any disclaimer, the term of this patent is extended or adjusted under 35 U.S.C. 154(b) by 264 days.

(21) Appl. No.: 14/001,065

(22) PCT Filed: Feb. 24, 2012

(86) PCT No.: PCT/JP2012/054506
§ 371 (c)(1),
(2), (4) Date: Aug. 22, 2013

(87) PCT Pub. No.: WO2012/115217
PCT Pub. Date: Aug. 30, 2012

(65) Prior Publication Data
US 2013/0327698 A1 Dec. 12, 2013

(30) Foreign Application Priority Data
Feb. 25, 2011 (JP) .................................. 2011-039980

(51) Int. Cl.
| | |
|---|---|
| *A61M 1/36* | (2006.01) |
| *B01J 20/22* | (2006.01) |
| *B01J 20/28* | (2006.01) |
| *B01J 20/32* | (2006.01) |

(52) U.S. Cl.
CPC ............ *A61M 1/3679* (2013.01); *B01J 20/22* (2013.01); *B01J 20/28004* (2013.01); *B01J 20/28016* (2013.01); *B01J 20/28023* (2013.01); *B01J 20/28052* (2013.01); *B01J 20/321* (2013.01); *B01J 20/3219* (2013.01); *B01J 20/3251* (2013.01); *B01J 20/3257* (2013.01); *B01J 20/3259* (2013.01); *B01J 20/3293* (2013.01); *B01J 2220/58* (2013.01)

(58) Field of Classification Search
CPC .. A61M 1/3679; B01J 20/22; B01J 20/28004; B01J 20/28016; B01J 20/28023; B01J 20/28052; B01J 20/321; B01J 20/3219; B01J 20/3251; B01J 20/3257; B01J 20/3259; B01J 20/3293; B01J 2220/58
USPC ......................................... 210/263; 502/401
See application file for complete search history.

(56) References Cited

U.S. PATENT DOCUMENTS

| | | | |
|---|---|---|---|
| 5,407,581 A | 4/1995 | Onodera et al. | |
| 2005/0250169 A1* | 11/2005 | Gonzalez ................. | C12Q 1/34 435/18 |
| 2006/0060533 A1* | 3/2006 | Miyazawa et al. ........... | 210/656 |
| 2009/0275874 A1 | 11/2009 | Shimagaki et al. | |
| 2010/0176051 A1 | 7/2010 | Shimagaki | |

FOREIGN PATENT DOCUMENTS

| | | |
|---|---|---|
| JP | 56-147710 A | 11/1981 |
| JP | 05-168706 | 7/1993 |
| JP | 05-168706 A | 7/1993 |
| JP | 07-080062 | 3/1995 |
| JP | 2591500 | 3/1996 |
| JP | 2003-052817 | 2/2003 |
| JP | 2006-312804 | 11/2006 |
| JP | 2010-253181 | 11/2010 |
| WO | 2008/022682 | 2/2008 |
| WO | 2009/057574 A1 | 5/2009 |

\* cited by examiner

*Primary Examiner* — Dirk Bass
(74) *Attorney, Agent, or Firm* — DLA Piper LLP (US)

(57) ABSTRACT

A carrier for blood component adsorption enables selective and efficient adsorption removal of granulocytes and monocytes and, at the same time, enables adsorption removal of inflammatory cytokines. The carrier for blood component adsorption includes a water-insoluble carrier having a surface to which a functional group(s) containing a silyl group and an amino group is/are introduced.

22 Claims, No Drawings

CARRIER FOR BLOOD COMPONENT ADSORPTION AND BLOOD COMPONENT ADSORPTION COLUMN

TECHNICAL FIELD

This disclosure relates to a carrier for blood component adsorption and a column for blood component adsorption.

BACKGROUND

Inflammatory cytokines are deeply involved in causes of inflammatory diseases such as systemic lupus erythematosus, rheumatoid arthritis, multiple sclerosis, ulcerative colitis and Crohn's disease, and it has been considered that these inflammatory diseases can be treated by inactivating inflammatory cytokines with biologicals such as low molecular drugs and antibodies. However, it is becoming clear that each inflammatory cytokine does not act alone on the site of inflammation, but a plurality of types of inflammatory cytokines synergistically act to cause development and progression of inflammatory diseases. Therefore, recent interest has focused on the effectiveness of leukocytapheresis, in which activated leukocytes as the source of inflammatory cytokines are removed from the blood.

Known examples of the method of removing activated leukocytes from the blood include a method wherein a column for removal of leukocytes, which column uses a fiber or head as a medium, is employed to carry out extracorporeal circulation of blood of the patient with an inflammatory disease to selectively remove activated leukocytes by adsorption. In terms of the medium to selectively adsorb granulocytes, there is a report wherein a bead having a certain level of irregularity in its surface is used as a medium (JP 2501500 B) and, in terms of the medium that adsorbs activated leukocytes and cytokines at the same time, there are reports wherein a nonwoven fabric or bead whose surface is modified with amino groups is used as a medium (JP 2006-312804 A and JP 7-080062 A).

However, known adsorption carriers used for selective adsorption of activated leukocytes cannot be said to have a sufficient adsorption capacity at present and, therefore, to increase the therapeutic effect of leukocytapheresis in an inflammatory disease patient, it is believed that the adsorption capacity needs to be improved especially for granulocytes and monocytes among leukocytes.

There is thus a need to provide a carrier for blood component adsorption that enables selective and efficient adsorption removal of granulocytes and monocytes and, at the same time, enables adsorption removal of inflammatory cytokines.

SUMMARY

We discovered a carrier for blood component adsorption that enables efficient adsorption removal of granulocytes and monocytes as well as inflammatory cytokines.

We thus provide a carrier for blood component adsorption and a column for blood component adsorption described in the (1) to (9) below.

(1) A carrier for blood component adsorption comprising a water-insoluble carrier having a surface to which a functional group(s) containing a silyl group and an amino group is/are introduced.

(2) The carrier for blood component adsorption according to the above-described (1), wherein the water-insoluble carrier has a proton adsorption capacity of $1.5 \times 10^{-5}$ to $3.0 \times 10^{-3}$ eq/g.

(3) The carrier for blood component adsorption according, to the above-described (1) or (2), wherein the silicon atom of the silyl group and the nitrogen atom of the amino group are linked together by an alkyl chain.

(4) The carrier for blood component adsorption according to the above-described (3), wherein the alkyl chain is an alkyl chain having not more than 6 carbon atoms.

(5) The carrier for blood component adsorption according to any one of the above-described (1) to (4), wherein the silyl group has an alkyl group and/or alkoxy group.

(6) The carrier for blood component adsorption according to the above-described (5), wherein the alkyl group is a methyl group or ethyl group.

(7) The carrier for blood component adsorption according to the above-described (5) or (6), wherein the alkoxy group is a methoxy group or ethoxy group.

(8) The carrier for blood component adsorption according to any one of the above-described (1) to (7), wherein the water-insoluble carrier is composed of a fiber or particle.

(9) The carrier for blood component adsorption according to the above-described (8), wherein the fiber has a fiber diameter of, or the particle has a particle diameter of, 0.5 to 20 µm.

(10) A column for blood component adsorption filled with the carrier for blood component adsorption according to any one of the above-described (1) to (9).

With the carrier for blood component adsorption, granulocytes and monocytes can be efficiently removed by adsorption from blood of a patient with an inflammatory disease, and inflammatory cytokines can also be removed by adsorption at the same time. Further, a column for blood component adsorption filled with the carrier for blood, component adsorption can be used for leukocytapheresis, and can produce a preferred therapeutic effect in treatment of a severe inflammatory disease.

DETAILED DESCRIPTION

The carrier for blood component adsorption comprises a water-insoluble carrier having a surface to which a functional group(s) containing a silyl group and an amino group is/are introduced.

The "carrier for blood component adsorption" means a material with which a blood component(s) can be removed from blood by adsorption.

The blood component means a component constituting blood, and examples of the blood component includes blood cell components such as erythrocytes, leukocytes and platelets; and humoral factors such as inflammatory cytokines. For the purpose of treatment of an inflammatory disease, leukocytes and inflammatory cytokines are preferably removed by adsorption.

The inflammatory cytokine means a protein which is secreted from a cell and transmits information to a specific cell. Examples of the inflammatory cytokine include interleukins, tumor necrosis factor-α, transforming growth factor beta, interferon-γ, angiogenic growth factors and immunosuppressive acidic protein.

The interleukin means a cytokine which is secreted from a leukocyte and functions for controlling the immune system, and examples of the interleukin include interleukin-1, interleukin-6 (hereinafter referred to as "IL-6"), interleukin-8 (hereinafter referred to as "IL-8"), interleukin-10 and interleukin-17.

The adsorption means a state where a blood component(s) is/are attached to the carrier for blood component adsorption, and detachment of the blood component(s) does not easily occur.

Examples of the "water-insoluble carrier" include polyolefins such as polyethylene and polypropylene; polyesters such as polyethylene terephthalate and polybutylene terephthalate; fluorinated polymers such as Teflon (registered trademark); polysulfone-based polymers such as poly (p-phenylene ether sulfone); polyetherimides; polyimides; polyamides; polyethers; polyphenylene sulfides; polystyrenes; and acrylic polymers; and materials prepared by blending or alloying of these macromolecular compounds. For easy introduction of a functional group to the surface of the water-insoluble carrier, polystyrenes are preferred and, in view of heat resistance or retention of the shape upon processing, polypropylene and polypropylene-polyethylene copolymers are preferred.

The "functional group containing a silyl group and an amino group" means a functional group containing at least one each of silyl group and amino group in the chemical structure of the functional group.

The "silyl group" means a functional group having the following chemical structure:

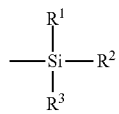

wherein the chemical structure of each of $R^1$, $R^2$ and $R^3$ is not limited, and each of $R^1$, $R^2$ and $R^3$ is preferably an alkyl group or alkoxy group, more preferably methyl, ethyl, methoxy or ethoxy. Examples of the silyl group wherein all of $R^1$, $R^2$ and $R^3$ are the same alkyl group include trimethylsilyl and triethylsilyl. Examples of the silyl group wherein all of $R^1$, $R^2$ and $R^3$ are the same alkoxy group include trimethoxysilyl and triethoxysilyl. Examples of the silyl group wherein $R^1$, $R^2$ and $R^3$ are a plurality of types of alkyl group(s) and/or alkoxy group(s) include methyldimethoxysilyl.

The silyl group may contain one or more siloxane bonds. However, in cases where siloxane bonds continue too much, free movement of the functional group is suppressed so that the number of continuous siloxane bonds is preferably not more than 5.

In cases where the silyl group described above is a silyl group wherein all of $R^1$, $R^2$ and $R^3$ are substituted by an alkyl group(s) and/or alkoxy group(s), the number of carbon atoms and oxygen atoms constituting the alkyl group(s) and/or alkoxy group(s) is preferably not more than 5 since, in this case, the silyl group can more easily interact with blood components.

The "amino group" means a functional group having the following structure:

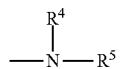

wherein the chemical structure of each of $R^4$ and $R^5$ is not limited, and examples of each of $R^4$ and $R^5$ include alkyl groups.

The structure in which both $R^4$ and $R^5$ are hydrogen is called a primary amino group; a structure in which one of $R^4$ and $R^5$ is a chemical structure other than hydrogen is called a secondary amino group; and a structure in which each of $R^4$ and $R^5$ is substituted by a chemical structure other than hydrogen is called a tertiary amino group.

The "amino group" herein include functional groups having the structure shown below, that is, quaternary ammonium groups:

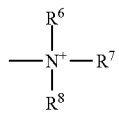

wherein each of $R^6$, $R^7$ and $R^8$ represents a chemical structure other than hydrogen, and the chemical structure is not limited. Examples of each of $R^6$, $R^7$ and $R^8$ include alkyl groups.

In cases where the functional group has an amino group at its terminus, that is, in cases where the functional group has a primary amino group, which is highly reactive, there is an increased risk of cross-linking of this amino group to another chemical structure contained, in the carrier for blood component adsorption and, moreover, the living body may be overstimulated by the amino group. Therefore, the amino group is preferably a secondary or tertiary amino group, or a quaternary ammonium group.

In the chemical structure of the functional group, the chemical structure between the silyl group and the amino group, that is, the chemical structure linking the silicon atom of the silyl group to the nitrogen atom of the amino group (hereinafter referred to as the spacer) is preferably constituted by a hydrogen atom(s), carbon atom(s), oxygen atom(s) and/or sulfur atom(s). In cases where the spacer is too large, the density of the silyl group is low, so that the number of atoms constituting the spacer is preferably not more than 200. The spacer is more preferably an alkyl chain, still more preferably an alkyl chain having not more than 6 carbon atoms.

Examples of the reactive functional group that mediates linking between the water-insoluble carrier and the above-described functional group when the "functional group containing a silyl group and an amino group" is to be introduced to the surface of the water-insoluble carrier include active halogen groups such as the halomethyl group, haloacetyl group, haloacetamidomethyl group and halogenated alkyl group; epoxide group; carboxyl group; isocyanate group; thioisocyanate group; and acid anhydride group. Active halogen groups are preferred, and the haloacetamidomethyl group is more preferred, since these have appropriate degrees of reactivity.

The above-described functional group wherein a silyl group is terminally positioned and the spacer is an alkyl chain can be obtained by, for example, reacting silylalkylamine, which is commercially easily available, with a haloacetamidomethyl group. For example, the above-described functional group wherein the spacer is an alkyl chain having 3 carbon atoms can be obtained by reacting 3-aminopropyltrimethoxysilane or 3-aminopropyltriethoxysilane with a haloacetamidomethyl group.

The form of the "water-insoluble carrier" is preferably a "fiber or particle" in view of enhancing the efficiency of removal of leukocytes by adsorption. In cases where the water-insoluble carrier is a fiber, the cross-section of the fiber may have a shape other than a true circle, an the fiber may be a hollow fiber. The "fiber diameter of the fiber" and "particle diameter of the particle" of the "fiber or particle"

are preferably 0.5 to 20 µm, more preferably 4 to 10 µm, in view of more stable exertion of the phagocytic activity of leukocytes. The lower limit is preferably 0.5 µm, more preferably 4 µm. The upper limit is preferably 20 µm, more preferably 10 µm. Either preferred lower limit may be combined with either preferred upper limit. The phagocytic activity of leukocytes herein means the property of granulocytes and monocytes to capture and eat microorganisms, bacteria and the like which, have invaded into the body of human or the like.

The "fiber diameter of the fiber" means the mean of values obtained by randomly collecting 10 samples of small pieces of the fiber and taking a photograph of each sample using a scanning electron microscope at a magnification of 2000×, followed by measuring the diameter of the fiber at 10 locations per photograph (100 locations in total). Similarly, the "particle diameter of the particle" means the mean of values obtained by randomly collecting 10 samples of small pieces of the particle and taking a photograph of each sample using a scanning electron microscope at a magnification of 2000×, followed by measuring the diameter of the particle at 10 locations per photograph (100 locations in total).

In cases where the fiber diameter of the fiber is less than 10 µm, a fiber having a larger diameter may be mixed in view of securing the strength of the carrier for blood component adsorption, and the fiber diameter of such a fiber having a larger diameter is preferably 10 to 50 µm.

Examples of the shape of the water-insoluble carrier composed of a fiber include a woven fabric, non-woven fabric, cotton cloth and hollow fiber. In cases where the shape is a non-woven fabric, a scaffold fiber such as polypropylene is also preferably included for maintaining the shape.

In cases where the carrier for blood component adsorption is composed of a fiber, removal of the blood component may be based on the principle of nitration. However, in consideration of suppression of the pressure loss due to clogging, granulocytes and monocytes are preferably removed by adsorption utilizing their phagocytic activity and the interaction with the "functional group containing a silyl group and an amino group", and inflammatory cytokines are preferably removed by adsorption utilizing the interaction with the "functional group containing, a silyl group and an amino group". In view of this, in cases where the carrier for blood component adsorption is used by filling a container such as a column with the carrier, the porosity may be increased. On the other hand, since, in cases where the porosity is too large, the shape of the adsorption carrier can be hardly maintained, the porosity of the water-insoluble carrier is preferably 85 to 98%, more preferably 90 to 95%. The lower limit of the value is preferably 85%, more preferably 90%. The upper limit of the value is preferably 98%, more preferably 95%. Either preferred lower limit may be combined with either preferred upper limit.

The "porosity" is the ratio of the volume of the void in the carrier for blood component adsorption, and means the percentage value calculated by dividing the volume of the void in the carrier for blood component adsorption by the apparent volume of the carrier for blood component adsorption. More specifically, a cross-sectional photograph of the carrier for blood component adsorption is taken using a scanning electron microscope at a magnification of 200×, and based on the result of image analysis of the photograph, the porosity is calculated according to the Equation 1 below:

$$\text{Porosity}(\%) = \{(b-a)/b\} \times 100 \qquad \text{Equation 1}$$

a: Area of the part occupied by the water-insoluble carrier
b: Total area of the cross-section of the carrier for blood component adsorption.

The silyl group contained in the "functional group containing a silyl group and an amino group" is assumed to contribute largely to selective adsorption of granulocytes and monocytes. On the other hand, it is considered that the presence of silyl groups at high density suppresses free movement of the functional group, leading to insufficient interaction with granulocytes and monocytes.

The amino group contained in the "functional group containing a silyl group and an amino group" is also assumed to contribute largely to selective adsorption of granulocytes and monocytes. On the other hand, it is assumed that the presence of amino groups at high density causes competitive adsorption with proteins having negative charges, leading to decreased adsorption rates of granulocytes and monocytes. The density of amino groups can be represented by the proton adsorption capacity, and the proton adsorption capacity of the carrier for blood component adsorption is preferably $1.5 \times 10^{-5}$ to $3.0 \times 10^{-3}$ eq/g, more preferably $1.0 \times 10^{-4}$ to $2.0 \times 10^{-3}$ eq/g. The lower limit of the value is preferably $1.5 \times 10^{-5}$ eq/g, more preferably $1.0 \times 10^{-4}$ eq/g. The upper limit of the value is preferably $3.0 \times 10^{-3}$ eq/g, more preferably $2.0 \times 10^{-3}$ eq/g. Either preferred lower limit may be combined with either preferred upper limit. An adsorption capacity of 1 eq/g herein means that 1 g of an adsorption carrier can adsorb 1 mol of protons.

The silyl group contained in the "functional group containing a silyl group and an amino group" is assumed to contribute also to adsorption of inflammatory cytokines to some extent. Although detailed mechanisms, are unknown, it is assumed that, since inflammatory cytokines are proteins of about 1 to several 10 kDa and contain many kinds of hydrophobic amino acids, inflammatory cytokines interact with, for example, hydrophobic silyl groups such as trimethylsilyl.

The container shape of the blood component adsorption column filled with the carrier for blood component adsorption is not limited as long as it has an inlet and an outlet for blood, and examples of the container include polygonal prism-shaped containers such as cylindrical, triangular prism-shaped, quadrangular prism-shaped, hexagonal prism-shaped and octagonal prism-shaped containers. The container is preferably a container which can be filled with the carrier for blood component adsorption in a laminated form, a container which can be filled with the carrier for blood component adsorption wound into a cylindrical shape, or a container wherein blood flows from the circumference of a cylinder into the inside thereof, followed by flowing to the outside of the container.

EXAMPLES

The column for blood component adsorption will now be described in more detail by way of experimental examples. In Examples, wt % represents % by weight.

(Preparation of Non-Woven Fabric Made of PP)

A sea-island composite fiber having 36 islands each of which further has a core/sheath complex was obtained using the following components under the conditions of a spinning rate of 800 m/minute and a draw ratio of 3.

Core component of the island: polypropylene
Sheath component of the island: 90 wt % polystyrene; and 10 wt % polypropylene
Sea component: copolymerized polyester comprising ethylene terephthalate units as major repeating units and 3 wt % 5-sodium sulfoisophthalic acid as a copolymerization component
Composite ratio (weight ratio); core:sheath:sea=45:40:15

After preparing a non-woven fabric composed of this fiber in an amount of 85 wt % and a polypropylene fiber having a diameter of 20 µm in an amount of 15 wt %, a sheet-shaped polypropylene net (thickness, 0.5 mm; single fiber diameter, 0.3 mm; aperture, 2 mm×2 mm) was sandwiched between two sheets of this non-woven fabric, and the resultant was needle-punched to obtain a non-woven fabric having a three-layer structure, (hereinafter referred to as the non-woven fabric made of PP).

(Preparation of Non-Woven Fabric Made of PSt+PP)

The non-woven fabric made of PP was treated at 95° C. with 3 wt % aqueous sodium hydroxide solution to dissolve the sea component. By this, a nonwoven fabric having a diameter of the core/sheath fiber of 5 μm and a bulk density of 0.02 g/cm$^3$ (non-woven fabric made of PSt+PP, hereinafter referred to as "the non-woven, fabric A") was prepared.

(Preparation of Chloroacetamidomethylated Non-Woven Fabric)

At not more than 10° C., 46 wt % nitrobenzene, 46 wt % sulfuric acid, 1 wt. % paraformaldehyde and 7 wt % N-methylol-α-chloroacetamide (hereinafter referred to as "NMCA") were mixed together, and the resulting mixture was stirred and dissolved, to prepare a reaction liquid, for NMCA modification. The temperature of this reaction liquid for NMCA modification was adjusted, to 5° C., and the reaction liquid for NMCA modification was added to the non-woven fabric A at a solid/liquid ratio corresponding to about 40 mL of the reaction liquid for NMCA modification with respect to 1 g of the non-woven fabric A. The reaction mixture was left to stand at 5° C. in a water bath to allow the reaction to proceed for 2 hours. Thereafter, the non-woven fabric was removed from the reaction liquid, and immersed in nitrobenzene in the same amount as the reaction liquid for NMCA treatment, for washing. Subsequently, the non-woven fabric was removed therefrom, and immersed in methanol for washing, to obtain a chloroacetamidomethylated non-woven fabric (hereinafter referred to as the "non-woven fabric B").

(Preparation of Tetraethylenepentamine-Modified Non-Woven Fabric)

Tetraethylenepentamine (hereinafter referred to as "TEPA") and triethylamine were dissolved in 500 mL of dimethyl sulfoxide (hereinafter referred to as DMSO) such that their concentrations are 20 mM and 473 mM, respectively. In the resulting solution, 10 g of the non-woven fabric B was immersed, and the reaction was allowed to proceed at 40° C. for 3 hours. The non-woven fabric after the reaction was washed with DMSO and methanol, and further with water, to obtain a TEPA-modified non-woven fabric (hereinafter referred to as the "non-woven fabric C"). The structural formula of the functional group introduced to the non-woven fabric C is shown in Table 1-1.

(Preparation of N-2-(Aminoethyl)-3-Aminopropyltrimethoxysilane-Modified Non-Woven Fabric)

To 46.5 mL of DMSO, 0.22 mL of N-2-(aminoethyl)-3-aminopropyltrimethoxysilane was added, and 3.3 mL of triethylamine was further added thereto, followed by mixing the resulting mixture to prepare a liquid. In this liquid, 1 g of the non-woven fabric B was immersed, and the reaction was allowed to proceed at 40° C. for 2 hours. The non-woven fabric after the reaction was washed with DMSO and methanol, and further with water, to obtain an N-2-(aminoethyl)-3-aminopropyltrimethoxysilane-modified non-woven fabric (hereinafter referred to as the "non-woven, fabric D"). The structural formula of the functional group introduced to the non-woven, fabric D is shown in Table 1.

(Preparation of N-2-(Aminoethyl)-3-Aminopropyltriethoxysilane-Modified Non-Woven Fabric)

To 46.5 mL of DMSO, 0.27 mL of N-2-(aminoethyl)-3-aminopropyltriethoxysilane was added, and 3.3 mL of triethylamine was further added thereto, followed by mixing the resulting mixture to prepare a liquid. In this liquid, 1 g of the non-woven fabric B was immersed, and the reaction was allowed to proceed at 40° C. for 2 hours. The non-woven fabric after the reaction was washed with DMSO and methanol, and further with water, to obtain an N-2-(aminoethyl)-3-aminopropyltriethoxysilane-modified non-woven fabric (hereinafter referred to as the "non-woven fabric E"). The structural formula of the functional group introduced to the non-woven fabric E is shown in Table 1.

(Preparation of N-2-(Aminoethyl)-3-Aminopropylmethyldimethoxysilane-Modified Non-Woven Fabric)

To 46.5 mL of DMSO, 0.21 mL of N-2-(aminoethyl)-3-aminopropylmethyldimethoxysilane was added, and 3.3 mL of triethylamine was further added thereto, followed by mixing the resulting mixture to prepare a liquid. In this liquid, 1 g of the non-woven fabric B was immersed, and the reaction was allowed to proceed at 40° C. for 2 hours. The non-woven fabric after the reaction was washed with DMSO and methanol, and further with water, to obtain an N-2-(aminoethyl)-3-aminopropylmethyldimethoxysilane-modified non-woven fabric (hereinafter referred to as the "non-woven fabric F"). The structural formula of the functional group introduced to the non-woven fabric F is shown in Table 1.

(Preparation of 3-Aminopropyltrimethoxysilane-Modified Non-Woven Fabric)

To 46.5 mL of DMSO, 0.18 mL of 3-aminopropyltrimethoxysilane was added, and 3.3 mL of triethylamine was further added thereto, followed by mixing the resulting mixture to prepare a liquid. In this liquid, 1 g of the non-woven fabric B was immersed, and the reaction was allowed to proceed at 40° C. for 2 hours. The non-woven fabric after the reaction was washed with DMSO and methanol, and further with water, to obtain a 3-aminopropyltrimethoxysilane-modified non-woven fabric (hereinafter referred to as the "non-woven fabric G"). The structural formula of the functional group introduced to the non-woven fabric G is shown in Table 1.

(Preparation of 3-Aminopropyltriethoxysilane-Modified Non-Woven Fabric)

To 46.5 mL of DMSO, 0.18 mL of 3-aminopropyltriethoxysilane was added, and 3.3 mL of triethylamine was further added thereto, followed by mixing the resulting mixture to prepare a liquid. In this liquid, 1 g of the non-woven fabric B was immersed, and the reaction was allowed to proceed at 40° C. for 2 hours. The non-woven fabric after the reaction was washed with DMSO and methanol, and further with water, to obtain a 3-aminopropyltriethoxysilane-modified non-woven fabric (hereinafter referred to as the "non-woven fabric H"). The structural formula of the functional group introduced to the non-woven fabric H is shown in Table 1.

(Preparation of 3-Ethoxypropylamine-Modified Non-Woven Fabric)

To 46.5 ml of DMSO, 0.12 mL of 3-ethoxypropylamine was added, and 3.3 mL of triethylamine was further added thereto, followed by mixing the resulting mixture to prepare a liquid. In this liquid, 1 g of the non-woven fabric B was immersed, and the reaction, was allowed to proceed at 40° C. for 2 hours. The non-woven fabric after the reaction was washed with DMSO and methanol, and further with water, to obtain, a 3-ethoxypropylamine-modified non-woven fabric (hereinafter referred to as the "non-woven fabric I"). The structural formula of the functional group introduced to the non-woven fabric I is shown in Table 1.

(Preparation of 4-Aminobutylaldehyde Dimethylacetal-Modified Non-Woven Fabric)

To 46.5 mL of DMSO, 0.14 mL of 4-aminobutylaldehyde dimethylacetal was added, and 3.3 mL of triethylamine was further added thereto, followed by mixing the resulting mixture to prepare a liquid. In this liquid, 1 g of the non-woven fabric B was immersed, and the reaction was allowed to proceed at 40° C. for 2 hours. The non-woven fabric after the reaction was washed with DMSO and methanol, and further with water, to obtain a 4-aminobutylaldehyde dimethylacetal-modified non-woven fabric (hereinafter referred to as the "non-woven fabric J"). The structural formula of the functional group introduced to the non-woven fabric J is shown in Table 1.

(Preparation of 3-Aminopropionaldehyde Diethylacetal-Modified Non-Woven Fabric)

To 46.5 mL of DMSO, 0.16 mL of 3-aminopropionaldehyde diethylacetal was added, and 3.3 mL of triethylamine was further added thereto, followed by mixing the resulting mixture to prepare a liquid. In this liquid, 1 g of the non-woven fabric B was immersed, and the reaction was allowed to proceed at 40° C. for 2 hours. The non-woven fabric after the reaction was washed with DMSO and methanol, and further with water, to obtain a 3-aminopropionaldehyde diethylacetal-modified non-woven fabric (hereinafter referred to as the "non-woven fabric K"). The structural formula of the functional group introduced to the non-woven fabric K is shown in Table 1.

(Preparation of Chloroacetamidomethylated Polysulfone)

To 32 mL of 5 wt % polysulfone/nitrobenzene solution, 2 mL of 2 wt % NMCA/sulfuric acid solution prepared at 0° C. was added, and the resulting mixture was stirred for 1 hour. To this mixture, 800 mL of ice-cold methanol was added to precipitate chloroacetamidomethylated polysulfone, which was then recovered. The recovered chloroacetamidomethylated polysulfone was dissolved in 20 mL of dimethylformamide (hereinafter referred to as "DMF"), and 400 mL of ice-cold methanol was added again to the resulting solution, to obtain chloroacetamidomethylated polysulfone.

(Preparation of Tetraethylenepentamine-Modified Polysulfone Non-Woven Fabric)

In 30 mL of DMF, 1 g of chloroacetamidomethylated polysulfone was dissolved, and tetraethylenepentamine was added to the resulting solution to a concentration of 20 mM. The resulting mixture was stirred for 17 hours, and 600 mL of ice-cold methanol was added thereto to precipitate tetraethylenepentamine-modified polysulfone, which was then, recovered. The recovered tetraethylenepentamine-modified polysulfone was dissolved again in 20 mL of DMF, and 0.1 g of the non-woven fabric A was immersed in the resulting solution. The non-woven fabric A was then immediately removed from the solution, and further immersed in methanol, to obtain a tetraethylenepentamine-modified polysulfone non-woven fabric (hereinafter referred to as the "non-woven fabric L"). The structural formula of the functional group introduced to the non-woven fabric L is shown in Table 1.

(Preparation of N-2-(Aminoethyl)-3-Aminopropyltrimethoxysilane-Modified Polysulfone Non-Woven Fabric)

In 30 mL of DMF, 1 g of chloroacetamidomethylated polysulfone was dissolved, and N-2-(aminoethyl)-3-aminopropyltrimethoxysilane was added to the resulting solution to a concentration of 20 mM. The resulting mixture was stirred for 17 hours, and 600 mL of ice-cold methanol was added thereto to precipitate N-2-(aminoethyl)-3-aminopropyltrimethoxysilane-modified polysulfone, which was then recovered. The recovered N-2-(aminoethyl)-3-aminopropyltrimethoxysilane-modified polysulfone was dissolved again in 20 mL of DMF, and 0.1 g of the non-woven fabric A was immersed in the resulting solution. The non-woven fabric A was then immediately removed from the solution, and further immersed in methanol, to obtain a N-2-(aminoethyl)-3-aminopropyltrimethoxysilane-modified polysulfone non-woven fabric (hereinafter referred to as the "non-woven fabric M"). The structural formula of the functional group introduced to the non-woven fabric M is shown in Table 1.

(Preparation of N-2-(Aminoethyl)-3-Aminopropyltriethoxysilane-Modified Polysulfone Non-Woven Fabric)

In 30 mL of DMF, 1 g of chloroacetamidomethylated polysulfone was dissolved, and N-2-(aminoethyl)-3-aminopropyltriethoxysilane was added to the resulting solution to a concentration of 20 mM. The resulting mixture was stirred for 17 hours, and 600 mL of ice-cold methanol was added thereto to precipitate N-2-(aminoethyl)-3-aminopropyltriethoxysilane-modified polysulfone, which was then recovered. The recovered N-2-(aminoethyl)-3-aminopropyltriethoxysilane-modified polysulfone was dissolved again in 20 mL of DMF, and 0.1 g of the non-woven fabric A was immersed in the resulting solution. The non-woven fabric A was then immediately removed from the solution, and further immersed in methanol, to obtain a N-2-(aminoethyl)-3-aminopropyltriethoxysilane-modified polysulfone non-woven fabric (hereinafter referred to as the "non-woven fabric N"). The structural formula of the functional group introduced to the non-woven fabric N is shown in Table 1.

(Preparation of N-2-(Aminoethyl)-3-Aminopropylmethyldimethoxysilane-Modified Polysulfone Non-Woven Fabric)

In 30 mL of DMF, 1 g of chloroacetamidomethylated polysulfone was dissolved, and N-2-(aminoethyl)-3-aminopropylmethyldimethoxysilane was added to the resulting solution to a concentration of 20 mM. The resulting mixture was stirred for 17 hours, and 600 mL of ice-cold methanol was added thereto to precipitate N-2-(aminoethyl)-3-aminopropylmethyldimethoxysilane-modified polysulfone, which was then recovered. The recovered N-2-(aminoethyl)-3-aminopropylmethyldimethoxysilane-modified polysulfone was dissolved again in 20 mL of DMF, and 0.1 g of the non-woven fabric A was immersed in the resulting solution. The non-woven fabric A was then immediately removed from the solution, and further immersed in methanol, to obtain a N-2-(aminoethyl)-3-aminopropylmethyldimethoxysilane-modified polysulfone non-woven fabric (hereinafter referred to as the "non-woven fabric O"). The structural formula of the functional group introduced to the non-woven fabric O is shown in Table 1.

(Preparation of 3-Aminopropyltrimethoxysilane-Modified Polysulfone Non-Woven Fabric)

In 30 mL of DMF, 1 g of chloroacetamidomethylated polysulfone was dissolved, and 3-aminopropyltrimethoxysilane was added to the resulting solution to a concentration of 20 mM. The resulting mixture was stirred for 17 hours, and 600 mL of ice-cold, methanol was added thereto to precipitate 3-aminopropyltrimethoxysilane-modified polysulfone, which was then recovered. The recovered 3-aminopropyltrimethoxysilane-modified polysulfone was dissolved again in 20 mL of DMF, and 0.1 g of the non-woven fabric A was immersed in the resulting solution. The non-woven fabric A was then immediately removed from the solution, and further immersed in methanol, to obtain a 3-aminopropyltrimethoxysilane-modified polysulfone non-woven fabric (hereinafter referred to as the "non-woven fabric P"). The structural formula of the functional group introduced to the non-woven fabric P is shown in Table 1.

(Preparation of 3-Aminopropyltriethoxysilane-Modified Polysulfone Non-Woven Fabric)

In 30 mL of DMF, 1 g of chloroacetamidomethylated polysulfone was dissolved, and 3-aminopropyltriethoxysilane was added to the resulting solution to a concentration of 20 mM. The resulting mixture, was stirred for 17 hours, and 600 mL of ice-cold methanol was added thereto to precipitate 3-aminopropyltriethoxysilane-modified polysulfone, which was then recovered. The recovered 3-aminopropyltriethoxysilane-modified polysulfone was dissolved again in 20 mL of DMF, and 0.1 g of the non-woven fabric A was immersed in the resulting solution. The non-woven fabric A was then immediately removed from the solution, and further immersed in methanol, to obtain a 3-aminopropyltriethoxysilane-modified polysulfone non-woven fabric (hereinafter referred to as the "non-woven fabric Q"). The structural formula of the functional group introduced to the non-woven fabric Q is shown in Table 1.

(Preparation of 3-Ethoxypropylamine-Modified Polysulfone Non-Woven Fabric)

In 30 mL of DMF, 1 g of chloroacetamidomethylated polysulfone was dissolved, and 3-ethoxypropylamine was added to the resulting solution to a concentration of 20 mM. The resulting mixture was stirred for 17 hours, and 600 mL of ice-cold methanol was added thereto to precipitate 3-ethoxypropylamine-modified polysulfone, which was then recovered. The recovered 3-ethoxypropylamine-modified polysulfone was dissolved again in 20 mL of DMF, and 0.1 g of the non-woven fabric A was immersed in the resulting solution. The non-woven fabric A was then immediately removed from the solution, and further immersed in methanol, to obtain a 3-ethoxypropylamine-modified polysulfone non-woven, fabric (hereinafter referred to as the "non-woven fabric R"). The structural formula of the functional group introduced to the non-woven fabric R is shown in Table 1.

(Preparation of 4-Aminobutylaldehyde Dimethylacetal-Modified Polysulfone Non-Woven Fabric)

In 30 mL of DMF, 1 g of chloroacetamidomethylated polysulfone was dissolved, and 4-aminobutylaldehyde dimethylacetal was added to the resulting solution to a concentration of 20 mM. The resulting mixture was stirred for 17 hours, and 600 mL of ice-cold methanol was added thereto to precipitate 4-aminobutylaldehyde dimethylacetal-modified polysulfone, which was then recovered. The recovered 4-aminobutylaldehyde dimethylacetal-modified polysulfone was dissolved again in 20 mL of DMF, and 0.1 g of the non-woven fabric A was immersed in the resulting solution. The non-woven fabric A was then immediately removed from the solution, and further immersed in methanol, to obtain a 4-aminobutylaldehyde dimethylacetal-modified polysulfone non-woven fabric (hereinafter referred to as the "non-woven fabric S"). The structural formula of the functional group introduced to the non-woven fabric S is shown in Table 1.

(Preparation of 3-Aminopropionaldehyde Diethylacetal-Modified Polysulfone Non-Woven Fabric)

In 30 mL of DMF, 1 g of chloroacetamidomethylated polysulfone was dissolved, and 3-aminopropionaldehyde diethylacetal was added to the resulting solution to a concentration of 20 mM. The resulting mixture was stirred for 17 hours, and 600 mL of ice-cold methanol was added thereto to precipitate 3-aminopropionaldehyde diethylacetal-modified polysulfone, which was then recovered. The recovered 3-aminopropionaldehyde diethylacetal-modified polysulfone was dissolved again in 20 mL of DMF, and 0.1 g of the non-woven fabric A was immersed in the resulting solution. The non-woven fabric A was then immediately removed from the solution, and further immersed in methanol, to obtain a 3-aminopropionaldehyde diethylacetal-modified polysulfone non-woven fabric (hereinafter referred to as the "non-woven fabric T"). The structural formula of the functional group introduced to the non-woven fabric T is shown in Table 1.

TABLE 1

| Non-woven fabric | Functional group introduced (Each wavy line represents the surface of a water-insoluble carrier) |
|---|---|
| Non-woven fabric C, L | 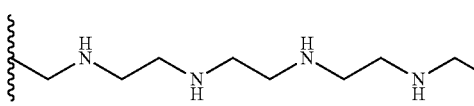 |
| Non-woven fabric D, M | 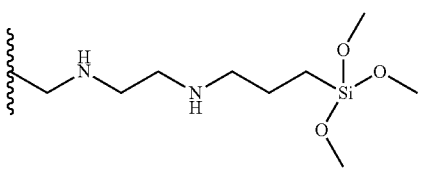 [SMILES: *CNCCNCCC[Si](OC)(OC)OC] |
| Non-woven fabric E, N | 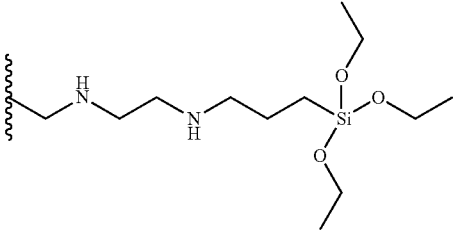 [SMILES: *CNCCNCCC[Si](OCC)(OCC)OCC] |

TABLE 1-continued

| Non-woven fabric | Functional group introduced (Each wavy line represents the surface of a water-insoluble carrier) |
|---|---|
| Non-woven fabric F, O | 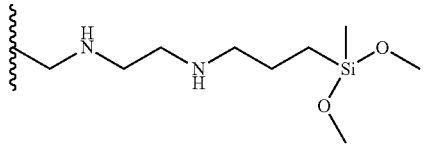 [SMILES: *CNCCNCCC[Si](C)(OC)OC] |
| Non-woven fabric G, P | 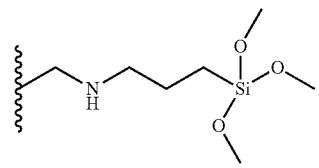 [SMILES: *CNCCC[Si](OC)(OC)OC] |
| Non-woven fabric H, Q | 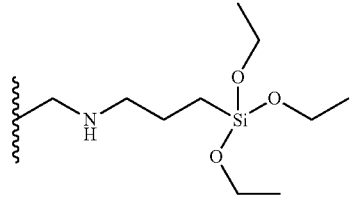 [SMILES: *CNCCC[Si](OCC)(OCC)OCC] |
| Non-woven fabric I, R | 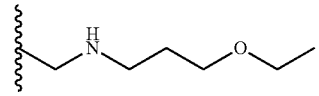 [SMILES: *CNCCCOCC] |
| Non-woven fabric J, S | 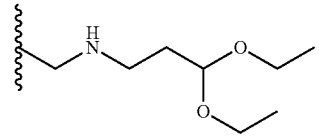 [SMILES: *CNCCC(OCC)OCC] |
| Non-woven fabric K, T | 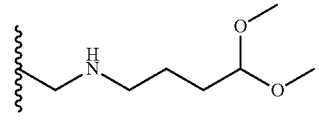 [SMILES: *CNCCCC(OC)OC] |

Example 1

The non-woven fabric D was cut out into a disk having a diameter of 8 mm, and placed in a polypropylene container. To this container, 1 mL of human blood (heparin concentration, 30 U/mL) was added, and the content of the container was mixed by inversion in an incubator at 37° C. for 20 minutes. Thereafter, the adsorption ratio of each blood component was calculated according to the Equations 2 to 4 below. Measurement of the number of each blood component was carried out using Automated Hematology Analyzer XT-1800i (Sysmex Corporation). The results are shown in Table 2.

Ratio of granulocyte adsorption(%)={(number of granulocytes in blood before circulation)−(number of granulocytes in blood after circulation)}/ (number of granulocytes in blood before circulation)×100   Equation 2

Ratio of monocyte adsorption(%)={(number of monocytes in blood before circulation)−(number of monocytes in blood after circulation)}/(number of monocytes in blood before circulation)× 100   Equation 3

Ratio of lymphocyte adsorption(%)={(number of lymphocytes in blood before circulation)−(number of lymphocytes in blood after circulation)}/ (number of lymphocytes in blood before circulation)×100   Equation 4

Example 2

The non-woven fabric E was cut out into a disk having a diameter of 8 mm, and placed in a polypropylene container. To this container, 1 mL of human blood (heparin concentration, 30 U/mL) was added, and the content of the container was mixed by inversion in an incubator at 37° C. for 20 minutes. Thereafter, the adsorption ratio of each blood component was calculated in the same manner as in Example 1. The results are shown in Table 2.

Example 3

The non-woven fabric F was cut out into a disk having a diameter of 8 mm, and placed in a polypropylene container. To this container, 1 mL of human blood (heparin concentration, 30 U/mL) was added, and the content of the container was mixed by inversion in an incubator at 37° C. for

Example 4

The non-woven fabric G was cut out into a disk having a diameter of 8 mm, and placed in a polypropylene container. To this container, 1 mL of human blood (heparin concentration, 30 U/mL) was added, and the content of the container was mixed by inversion in an incubator at 37° C. for 20 minutes. Thereafter, the adsorption ratio of each blood component was calculated in the same manner as in Example 1. The results are shown in Table 2.

Example 5

The non-woven fabric H was cut out into a disk having a diameter of 8 mm, and placed in a polypropylene container. To this container, 1 mL of human blood (heparin concentration, 30 U/mL) was added, and the content of the container was mixed by inversion in an incubator at 37° C. for 20 minutes. Thereafter, the adsorption ratio of each blood component was calculated in the same manner as in Example 1. The results are shown in Table 2.

Example 6

The non-woven fabric M was cut out into a disk having a diameter of 8 mm, and placed in a polypropylene container. To this container, 1 mL of human blood (heparin concentration, 30 U/mL) was added, and the content of the container was mixed by inversion in an incubator at 37° C. for 20 minutes. Thereafter, the adsorption ratio of each blood component was calculated in the same manner as in Example 1. The results are shown in Table 2.

Example 7

The non-woven fabric N was cut out into a disk having a diameter of 8 mm, and placed in a polypropylene container. To this container, 1 mL of human, blood (heparin concentration, 30 U/mL) was added, and the content of the container was mixed by inversion in an incubator at 37° C. for 20 minutes. Thereafter, the adsorption ratio of each blood component was calculated in the same manner as in Example 1. The results are shown in Table 2.

Example 8

The non-woven fabric O was cut out into a disk having a diameter of 8 mm, and placed in a polypropylene container. To this container, 1 mL of human blood (heparin concentration, 30 U/mL) was added, and the content of the container was mixed by inversion in an incubator at 37° C. for 0.20 minutes. Thereafter, the adsorption ratio of each blood component was calculated in the same manner as in Example 1. The results are shown in Table 2.

Example 9

The non-woven fabric P was cut out into a disk having a diameter of 8 mm, and placed in a polypropylene container. To this container, 0.1 mL of human blood (heparin concentration, 30 U/mL) was added, and the content of the container was mixed by inversion, in an incubator at 37° C. for 20 minutes. Thereafter, the adsorption ratio of each blood component was calculated in the same manner as in Example 1. The results are shown in Table 2.

Example 10

The non-woven fabric Q was cut out into a disk having a diameter of 8 mm, and placed in a polypropylene container. To this container, 1 mL of human blood (heparin concentration, 30 U/mL) was added, and the content of the container was mixed by inversion in an incubator at 37° C. for 20 minutes. Thereafter, the adsorption ratio of each blood component was calculated in the same manner as in Example 1. The results are shown in Table 2.

Comparative Example 1

The non-woven fabric C was cut out into a disk having a diameter of 8 mm, and placed in a polypropylene container. To this container, 1 mL of human blood (heparin concentration, 30 U/mL) was added, and the content of the container was mixed by inversion in an incubator at 37° C. for 20 minutes. Thereafter, the adsorption ratio of each blood component was calculated in the same manner as m Example 1. The results are shown in Table 2.

Comparative Example 2

The non-woven fabric I was cut out into a disk having a diameter of 8 mm, and placed in a polypropylene container. To this container, 1 mL of human blood (heparin concentration, 30 U/mL) was added, and the content of the container was mixed by inversion in an incubator at 37° C. for 20 minutes. Thereafter, the adsorption ratio of each blood component was calculated in the same manner as in Example 1. The results are shown in Table 2.

Comparative Example 3

The non-woven fabric J was cut out into a disk having a diameter of 8 mm, and placed in a polypropylene container. To this container, 1 mL of human blood (heparin concentration, 30 U/mL) was added, and the content of the container was mixed by inversion in an incubator at 37° C. for 20 minutes. Thereafter, the adsorption ratio of each blood component was calculated in the same manner as in Example 1. The results are shown in Table 2.

Comparative Example 4

The non-woven fabric K was cut out into a disk having a diameter of 8 mm, and placed in a polypropylene container. To this container, 1 mL of human blood (heparin concentration, 30 U/mL) was added, and the content of the container was mixed by inversion in an incubator at 37° C. for 20 minutes. Thereafter, the adsorption ratio of each blood component was calculated in the same manner as in Example 1. The results are shown in Table 2.

Comparative Example 5

The non-woven fabric L was cut out into a disk having a diameter of 8 mm, and placed in a polypropylene container. To this container, 1 mL of human blood (heparin concentration, 30 U/mL) was added, and the content of the container was mixed by inversion in an incubator at 37° C. for 20 minutes. Thereafter, the adsorption ratio of each blood component was calculated in the same manner as in Example 1. The results are shown in Table 2.

Comparative Example 6

The non-woven fabric R was cut out into a disk having a diameter of 8 mm, and placed in a polypropylene container. To this container, 1 mL of human, blood (heparin concentration, 30 U/mL) was added, and the content of the container was mixed by inversion in an incubator at 37° C. for 20 minutes. Thereafter, the adsorption ratio of each blood component was calculated in the same manner as in Example 1. The results are shown in Table 2.

Comparative Example 7

The non-woven fabric S was cut out into a disk having a diameter of 8 mm, and placed in a polypropylene container. To this container, 1 mL of human blood (heparin concentration, 30 U/mL) was added, and the content of the container was mixed by inversion in an incubator at 37° C. for 20 minutes. Thereafter, the adsorption ratio of each blood component was calculated in the same manner as in Example 1. The results are shown in Table 2.

Comparative Example 8

The non-woven fabric T was cut out into a disk having a diameter of 8 mm, and placed, in a polypropylene container. To this container, 1 mL of human blood (heparin concentration, 30 U/mL) was added, and the content of the container was mixed by inversion in an incubator at 37° C. for 20 minutes. Thereafter, the adsorption, ratio of each blood component was calculated in the same manner as in Example 1. The results are shown in Table 2.

Example 11

The non-woven fabric D was cut out into 2 disks each having a diameter of 8 mm, and placed in a polypropylene container. To this container, 0.8 mL of fetal bovine serum (hereinafter referred to as FBS) prepared such that each of IL-6 and IL-8 is contained at a concentration of 500 pg/mL was added, and the content of the container was mixed by inversion in an incubator at 37° C. for 1 hour. Thereafter, the remaining concentration of each of IL-6 and IL-8 was measured by the ELISA method, to calculate the adsorption, ratios of IL-6 and IL-8 according to the Equations 5 and 6, respectively. The results are shown in Table 2.

Ratio of IL-6 adsorption(%)={(concentration of IL-6 before mixing by inversion)−(concentration of IL-6 after mixing by inversion)}/(concentration of IL-6 before mixing by inversion)×100   Equation 5

Ratio of IL-8 adsorption(%)={(concentration of IL-8 before mixing by inversion)−(concentration of IL-8 after mixing by inversion)}/(concentration of IL-8 before mixing by inversion)×100   Equation 6

Example 12

The non-woven fabric E was cut out into 2 disks each having a diameter of 8 mm, and placed in a polypropylene container. To this container, 0.8 mL of FBS prepared such that each of IL-6 and IL-8 is contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 9. The results are shown in table 2.

Example 13

The non-woven fabric F was cut out into 2 disks each having a diameter of 8 mm, and placed in a polypropylene container. To this container, 0.8 mL of FBS prepared such that each of IL-6 and IL-8 is contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 9. The results are shown in Table 2.

Example 14

The non-woven fabric G was cut out into 2 disks each having a diameter of 8 mm, and placed in a polypropylene container. To this container, 0.8 mL of FBS prepared such that each of IL-6 and IL-8 is contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 9. The results are shown in Table 2.

Example 15

The non-woven fabric H was cut out into 2 disks each having a diameter of 8 mm, and placed in a polypropylene container. To this container, 0.8 mL of FBS prepared such that each, of IL-6 and IL-8 is contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 9. The results are shown in Table 2.

Example 16

The non-woven fabric M was cut out into 2 disks each having a diameter of 8 mm, and placed in a polypropylene container. To this container, 0.8 mL of FBS prepared such that each of IL-6 and IL-8 is contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 9. The results are shown in Table 2.

Example 17

The non-woven fabric N was cut out into 2 disks each having a diameter of 8 mm, and placed in a polypropylene container. To this container, 0.8 mL of FBS prepared such that each of IL-6 and IL-8 is contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 9. The results are shown in Table 2.

Example 18

The non-woven fabric O was cut out into 2 disks each having a diameter of 8 mm, and placed in a polypropylene container. To this container, 0.8 mL of FBS prepared such that each of IL-6 and IL-8 is contained at a concentration of 500 pg/mL was added, and the content of the container was mixed by inversion in an incubator at 37° C. for 1 hour. Thereafter, the adsorption ratios of IL-6 and IL-8 were, calculated in the same manner as in Example 9. The results are shown in Table 2.

Example 19

The non-woven fabric P was cut out info 2 disks each having a diameter of 8 mm, and placed in a polypropylene container. To this container, 0.8 mL of FBS prepared, such that each of IL-6 and IL-8 is contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 9. The results are shown in Table 2.

Example 20

The non-woven fabric Q was cut out into 2 disks each having a diameter of 8 mm, and placed in a polypropylene container. To this container, 0.8 mL of FBS prepared such that each of IL-6 and IL-8 is contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 9. The results are shown in Table 2.

Comparative Example 9

The non-woven fabric C was cut out into 2 disks each having a diameter of 8 mm, and placed in a polypropylene container. To this container, 0.8 mL of FBS prepared such that each of IL-6 and IL-8 is contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 9. The results are shown in Table 2.

Comparative Example 10

The non-woven fabric I was cut out into 2 disks each having a diameter of 8 mm, avid placed in a polypropylene container. To this container, 0.8 mL of FBS prepared such that each of IL-6 and IL-8 is contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 9. The results are shown in table 2.

Comparative Example 11

The non-woven fabric J was cut out into 2 disks each having a diameter of 8 mm, and placed in a polypropylene container. To this container, 0.8 mL of FBS prepared such that each of IL-6 and IL-8 is contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 9. The results are shown in Table 2.

Comparative Example 12

The non-woven fabric K was cut out into 2 disks each having a diameter of 8 mm, and placed in a polypropylene container. To this container, 0.8 mL of FBS prepared such that each of IL-6 and IL-8 is contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 9. The results are shown in Table 2.

Comparative Example 13

The non-woven fabric L was cut out into 2 disks each having a diameter of 8 mm, and placed in a polypropylene container. To this container, 0.8 mL of FBS prepared such that each of IL-6 and IL-8 is contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 9. The results are shown in Table 2.

Comparative Example 14

The non-woven fabric R was cut out into 2 disks each having a diameter of 8 mm, and placed in a polypropylene container. To this container, 0.8 mL of FBS prepared such that each of IL-6 and IL-8 is contained at a concentration of 500 pg/mL was added, and the content of the container was mixed by inversion in an incubator at 37° C. for 1 hour. Thereafter, the adsorption ratios of IL-6 mid IL-8 were calculated in the same manner as in Example 9. The results are shown in Table 2.

Comparative Example 15

The non-woven fabric S was cut out into 2 disks each having a diameter of 8 mm, and placed in a polypropylene container. To this container, 0.8 mL of FBS prepared such that each of IL-6 and IL-8 is contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 9. The results are shown in Table 2.

Comparative Example 16

The non-woven fabric T was cut out into 2 disks each having a diameter of 8 mm, and placed in a polypropylene container. To this container, 0.8 mL of FBS prepared such that each of IL-6 and IL-8 is contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 9. The results are shown in Table 2.

TABLE 2

| Sample (Non-woven fabric) | | Granulocyte adsorption ratio % | Lymphocyte adsorption ratio % | Monocyte adsorption ratio % | IL-6 adsorption ratio % | IL-8 adsorption ratio % |
|---|---|---|---|---|---|---|
| Examples 1 and 11 | Non-woven fabric D | 75.6 | 0.0 | 92 | 95.5 | 74.9 |
| Examples 2 and 12 | Non-woven fabric E | 86.5 | 0.0 | 91 | 91.3 | 49.9 |
| Examples 3 and 13 | Non-woven fabric F | 89.0 | 0.0 | 94 | 96.9 | 85.9 |
| Examples 4 and 14 | Non-woven fabric G | 80.4 | 0.0 | 92 | 88.4 | 60.2 |
| Examples 5 and 15 | Non-woven fabric H | 89.5 | 0.0 | 93 | 85.3 | 40.2 |
| Examples 6 and 16 | Non-woven fabric M | 80.2 | 0.0 | 95 | 92.2 | 80.3 |
| Examples 7 and 17 | Non-woven fabric N | 85.0 | 0.1 | 93 | 94.2 | 54.0 |
| Examples 8 and 18 | Non-woven fabric O | 86.5 | 0.0 | 95 | 95.4 | 90.0 |
| Examples 9 and 19 | Non-woven fabric P | 82.0 | 0.0 | 90 | 90.4 | 55.0 |
| Examples 10 and 20 | Non-woven fabric Q | 85.4 | 0.0 | 92 | 91.2 | 45.5 |
| Comparative Examples 1 and 9 | Non-woven fabric C | 66.8 | 0.0 | 73 | 96.9 | 79.3 |
| Comparative Examples 2 and 10 | Non-woven fabric I | 92.0 | 0.0 | 95 | 14.5 | 11.8 |
| Comparative Examples 3 and 11 | Non-woven fabric J | 88.0 | 0.0 | 94 | 43.8 | 3.1 |
| Comparative Examples 4 and 12 | Non-woven fabric K | 52.0 | 0.0 | 56 | 5.8 | 11.3 |
| Comparative Examples 5 and 13 | Non-woven fabric L | 70.2 | 0.1 | 75 | 95.0 | 85.3 |
| Comparative Examples 6 and 14 | Non-woven fabric R | 82.5 | 0.0 | 94 | 10.4 | 8.5 |
| Comparative Examples 7 and 15 | Non-woven fabric S | 75.2 | 0.2 | 94 | 35.2 | 5.5 |
| Comparative Examples 8 and 16 | Non-woven fabric T | 50.0 | 0.0 | 52 | 12.3 | 15.0 |

Based on the results shown in Table 2, it became clear that our carriers for blood component adsorption comprising a water-insoluble carrier having a surface to which a functional group containing a silyl group is introduced have higher adsorption ratios of granulocytes and monocytes as well as higher adsorption ratios of IL-6 and IL-8 compared to the carriers comprising a water-insoluble carrier having a surface whose functional group does not contain a silyl group.

INDUSTRIAL APPLICABILITY

Our carriers can be used as a blood component adsorption column in the field of medicine.

The invention claimed is:
1. A carrier for blood component adsorption comprising a water-insoluble carrier having a surface to which a functional group(s) containing a silyl group and an amino group is/are introduced, wherein said silyl group is terminally positioned in both the functional group and the water-insoluble carrier, wherein said water-insoluble carrier is polyolefin, fluorinated polymer, polysulfone-based polymer, polyetherimide, polyimide, polyamide, polyether, polyphenylene sulfide, polystyrene, acrylic polymer or a blend or alloy thereof, and wherein the water-insoluble carrier is functionalized with a reactive functional group(s) reactive with said amino group before introducing the functional group(s) containing the silyl group and the amino group to the carrier, wherein the reactive functional group(s) is selected from the group consisting of halomethyl group, haloacetyl group, haloacetamidomethyl group and halogenated alkyl group, epoxide group, isocyanate group, thioisocyanate group and acid anhydride group.

2. The carrier according to claim 1, wherein said water-insoluble carrier has a proton adsorption capacity of $1.5 \times 10^{-5}$ to $3.0 \times 10^{-3}$ eq/g.

3. The carrier according to claim 1, wherein the silicon atom of said silyl group and the nitrogen atom of said amino group are linked together by an alkyl chain.

4. The carrier according to claim 3, wherein said alkyl chain is an alkyl chain having not more than 6 carbon atoms.

5. The carrier according to claim 1, wherein said silyl group has an alkyl group and/or alkoxy group.

6. The carrier according to claim 5, wherein said alkyl group is a methyl group or ethyl group.

7. The carrier according to claim 5, wherein said alkoxy group is a methoxy group or ethoxy group.

8. The carrier according to claim 1, wherein said water-insoluble carrier is composed of a fiber or particle.

9. The carrier according to claim 8, wherein said fiber has a fiber diameter of, or said particle has a particle diameter of, 0.5 to 20 µm.

10. A column for blood component adsorption filled with the carrier for blood component adsorption according to claim 1.

11. The carrier according to claim 2, wherein the silicon atom of said silyl group and the nitrogen atom of said amino group are linked together by an alkyl chain.

12. The carrier according to claim 2, wherein said silyl group has an alkyl group and/or alkoxy group.

13. The carrier according to claim 3, wherein said silyl group has an alkyl group and/or alkoxy group.

14. The carrier according to claim 4, wherein said silyl group has an alkyl group and/or alkoxy group.

15. The carrier according to claim 6, wherein said alkoxy group is a methoxy group or ethoxy group.

16. The carrier according to claim 2, wherein said water-insoluble carrier is composed of a fiber or particle.

17. The carrier according to claim 3, wherein said water-insoluble carrier is composed of a fiber or particle.

18. The carrier according to claim 4, wherein said water-insoluble carrier is composed of a fiber or particle.

19. The carrier according to claim 5, wherein said water-insoluble carrier is composed of a fiber or particle.

20. The carrier according to claim 6, wherein said water-insoluble carrier is composed of a fiber or particle.

21. The carrier according to claim 1, wherein said water-insoluble carrier is poly(p phenylene ether sulfone) or an alloy of polystyrene and polypropylene.

22. The carrier according to claim 1, wherein said amino group is a secondary or tertiary amino group, or a quaternary ammonium group.

* * * * *